US012810577B2

(12) United States Patent
Galeotti et al.

(10) Patent No.: US 12,810,577 B2
(45) Date of Patent: Nov. 24, 2026

(54) SYSTEM, METHOD, AND COMPUTER PROGRAM PRODUCT FOR EXTRACTING FEATURES FROM IMAGING BIOMARKERS WITH MACHINE-LEARNING MODELS

(71) Applicant: Carnegie Mellon University, Pittsburgh, PA (US)

(72) Inventors: John Michael Galeotti, Pittsburgh, PA (US); Gautam Rajendrakumar Gare, Pittsburgh, PA (US); Ricardo Luis Rodriguez, Baltimore, MD (US); Bennett DeBoisblanc, New Orleans, LA (US)

(73) Assignee: Carnegie Mellon University, Pittsburgh, PA (US)

( * ) Notice: Subject to any disclaimer, the term of this patent is extended or adjusted under 35 U.S.C. 154(b) by 342 days.

(21) Appl. No.: 18/289,588

(22) PCT Filed: May 9, 2022

(86) PCT No.: PCT/US2022/028289
§ 371 (c)(1),
(2) Date: Nov. 6, 2023

(87) PCT Pub. No.: WO2022/236160
PCT Pub. Date: Nov. 10, 2022

(65) Prior Publication Data

US 2024/0249498 A1 Jul. 25, 2024

Related U.S. Application Data

(60) Provisional application No. 63/185,744, filed on May 7, 2021, provisional application No. 63/185,723, filed on May 7, 2021.

(51) Int. Cl.
*G06K 9/66* (2006.01)
*G06T 7/00* (2017.01)
(Continued)

(52) U.S. Cl.
CPC ............ *G06V 10/44* (2022.01); *G06T 7/0012* (2013.01); *G16H 30/20* (2018.01); *G16H 30/40* (2018.01);
(Continued)

(58) Field of Classification Search
CPC .... G06V 10/44; G06V 10/454; G06V 10/764; G06V 10/7784; G06V 2201/03;
(Continued)

(56) References Cited

U.S. PATENT DOCUMENTS 10,957,041 B2 * 3/2021 Yip ........................ G06N 3/045
11,551,357 B2 * 1/2023 Locke .................... G06V 10/25
(Continued)

FOREIGN PATENT DOCUMENTS

CA 3144315 A1 * 12/2020 ........... G06F 18/241
EP 3477555 A1 * 5/2019 ............. G06N 3/045

*Primary Examiner* — Xin Jia
(74) *Attorney, Agent, or Firm* — The Webb Law Firm

(57) ABSTRACT

Provided are systems, methods, and computer program products for extracting features from imaging biomarkers with machine-learning models. The method includes training a first artificial intelligence (AI) model based on first training data including images labeled with imaging biomarkers, the first AI model trained to identify a plurality of imaging biomarker features in at least one image, training a second AI model based on second training data including sets of imaging biomarker features associated with task-specific labels, the second AI model trained to identify at least one task-specific feature based at least partially on a set of imaging biomarker features, processing at least one input image with the first AI model to generate a first AI model output, and processing the first AI model output with the second AI model to generate a second AI model output.

19 Claims, 6 Drawing Sheets

(51) Int. Cl.
*G06V 10/44* (2022.01)
*G16H 30/20* (2018.01)
*G16H 30/40* (2018.01)

(52) U.S. Cl.
CPC ............... *G06T 2207/10132* (2013.01); *G06T 2207/20081* (2013.01); *G06T 2207/30061* (2013.01)

(58) Field of Classification Search
CPC ......... G06T 7/0012; G06T 2207/10132; G06T 2207/20081; G06T 2207/30061; G06T 2207/20084; G16H 30/20; G16H 30/40; G16H 50/20; G16H 50/70; G06N 3/0464; G06N 3/0895; G06N 3/09; G06N 3/096; G06N 3/045
See application file for complete search history.

(56) References Cited

U.S. PATENT DOCUMENTS

2020/0054306 A1 2/2020 Mehanian et al.
2022/0061813 A1* 3/2022 Halmann ............. A61B 8/5253

* cited by examiner

| | | | | | |
|---|---|---|---|---|---|
| (Sub) A-lines = | none | weak | bold | *also* stacked | *also* wide (> 2cm) |
| B-lines = | none | few (1-3) | some (4-6) | many\|coalescing | "white" (no striations) |
| B-lines origin = | N/A | pleura | sub-plu | | |
| Pleural thickness = | <1mm | 2-3mm | 4-5mm | >5mm | |
| Pleural location = | top-1/3rd | mid-1/3rd | btm-1/3rd | | |
| Sliding Pleural indent = | none | <5mm (few) | <5mm (multiple) | 5-10mm | >10mm |
| Sliding Pleural break = | none | <5mm (few) | <5mm (multiple) | 5-10mm | >10mm |
| Consolidation = | none | <5mm (few) | <5mm (multiple) | 5-10mm | >10mm |
| Effusion = | none | <5mm | >5mm | | |

500

FIG. 5

SYSTEM, METHOD, AND COMPUTER PROGRAM PRODUCT FOR EXTRACTING FEATURES FROM IMAGING BIOMARKERS WITH MACHINE-LEARNING MODELS

CROSS REFERENCE TO RELATED APPLICATIONS

This application is the United States national phase of International Application No. PCT/US22/28289, filed May 9, 2022, and claims priority to U.S. Provisional Patent Application No. 63/185,723, filed May 7, 2021, and U.S. Provisional Patent Application No. 63/185,744, filed May 7, 2021, the disclosures of which are hereby incorporated by reference in their entireties.

GOVERNMENT LICENSE RIGHTS

This invention was made with United States Government support under FA8750-17-2-0130 awarded by the Air Force Research Laboratory and W81XWH-19-C0083 awarded by U.S. Army Medical Research and Development Command. The United States Government has certain rights in the invention.

BACKGROUND

1. Field

This disclosure relates generally to imaging biomarkers and, in non-limiting embodiments, to systems, methods, and computer program products for extracting features from imaging biomarkers with machine-learning models.

2. Technical Considerations

Medical diagnostics often involves the identification and analysis of various diagnostic indicators called biomarkers that can help understand the underlying pathology to inform patient care. Existing approaches to use artificial neural networks (ANNs) for such diagnostics involving training models end-to-end from input images/videos to output metrics regarding a downstream task. By nature of this task specific training, the learned features are task-specific and do not readily generalize to other tasks. These task-specific models require retraining or transfer learning to adapt to new end tasks, such as recognizing visual features that are generally clinically relevant, since such visual features that were learned from other tasks are typically insufficient by themselves for the new task(s) of outputting new metrics. As a result, artificial intelligence (AI) models instead learn a combination of useful and misleading features which leads to poor model generalization.

The possibility of an AI model learning to base its output metrics on non-relevant visual features (that may have seemed relevant to the AI model during training) is especially harmful in life-and-death situations such as medicine and autonomous vehicles. A strategy to overcome this is to train with a large corpus of data to provide many diverse samples to help enforce the relevant visual features to the model and to gradually "train away" the misleading features. Unfortunately, such training strategies lead to very task-specific models. These models may perform well on the intended task when giving input data that is similar to at least some of the training data, but are not easily extensible to other related tasks. Even for their original task, these models can perform poorly on different input data that was not well represented in the training dataset.

SUMMARY

According to non-limiting embodiments or aspects, provided is a method comprising: training a first artificial intelligence (AI) model based on first training data comprising images labeled with imaging biomarkers, the first AI model trained to identify a plurality of imaging biomarker features in at least one image; training a second AI model based on second training data comprising sets of imaging biomarker features associated with task-specific labels, the second AI model trained to identify at least one task-specific feature based at least partially on a set of imaging biomarker features; processing at least one input image with the first AI model to generate a first AI model output; and processing the first AI model output with the second AI model to generate a second AI model output.

In non-limiting embodiments or aspects, each imaging biomarker feature of the plurality of imaging biomarker features comprises at least one value corresponding to a specific aspect of the at least one image or video including the at least one image. In non-limiting embodiments or aspects, the first AI model output comprises a set of imaging biomarker features, and the second AI model output comprises at least one task-specific feature. In non-limiting embodiments or aspects, the task-specific labels comprise severity metrics. In non-limiting embodiments or aspects, the first AI model is configured to process a sequence of images to identify the plurality of imaging biomarker features. In non-limiting embodiments or aspects, further comprising: generating the first training data based on annotations selected from a plurality of options presented on at least one graphical user interface. In non-limiting embodiments or aspects, the method further comprises: generating the second training data based on user input associating the task-specific labels with imaging-biomarker inputs. In non-limiting embodiments or aspects, the second AI model is configured to identify the at least one task-specific feature based at least partially on at least one of the following: the at least one input image, the at least one image, a video including the at least one image, an output of an image or video processing algorithm based on the at least one image or a video including the at least one image, or any combination thereof. In non-limiting embodiments or aspects, the plurality of imaging biomarker features comprises at least one of the following features of at least one ultrasound image: A-line, B-line, pleural line irregularity, or any combination thereof. In non-limiting embodiments or aspects, the plurality of imaging biomarkers is predefined.

According to non-limiting embodiments or aspects, provided is a system comprising: at least one computing device programmed or configured to: train a first artificial intelligence (AI) model based on first training data comprising images labeled with imaging biomarkers, the first AI model trained to identify a plurality of imaging biomarker features in at least one image; train a second AI model based on second training data comprising sets of imaging biomarker features associated with task-specific labels, the second AI model trained to identify at least one task-specific feature based at least partially on a set of imaging biomarker features; process at least one input image with the first AI model to generate a first AI model output; and process the first AI model output with the second AI model to generate a second AI model output.

In non-limiting embodiments or aspects, each imaging biomarker feature of the plurality of imaging biomarker features comprises at least one value corresponding to a specific aspect of the at least one image or video including the at least one image. In non-limiting embodiments or aspects, the first AI model output comprises a set of imaging biomarker features, and the second AI model output comprises at least one task-specific feature. In non-limiting embodiments or aspects, the task-specific labels comprise severity metrics. In non-limiting embodiments or aspects, the first AI model is configured to process a sequence of images to identify the plurality of imaging biomarker features. In non-limiting embodiments or aspects, the at least one computing device is further programmed or configured to: generate the first training data based on annotations selected from a plurality of options presented on at least one graphical user interface. In non-limiting embodiments or aspects, the at least one computing device is further programmed or configured to: generate the second training data based on user input associating the task-specific labels with imaging-biomarker inputs. In non-limiting embodiments or aspects, the second AI model is configured to identify the at least one task-specific feature based at least partially on at least one of the following: the at least one input image, the at least one image, a video including the at least one image, an output of an image or video processing algorithm based on the at least one image or a video including the at least one image, or any combination thereof. In non-limiting embodiments or aspects, the plurality of imaging biomarker features comprises at least one of the following features of at least one ultrasound image: A-line, B-line, pleural line irregularity, or any combination thereof.

In non-limiting embodiments or aspects, provided is a computer program product comprising at least one non-transitory computer-readable medium including program instructions that, when executed by at least one computing device, cause the at least one computing device to: train a first artificial intelligence (AI) model based on first training data comprising images labeled with imaging biomarkers, the first AI model trained to identify a plurality of imaging biomarker features in at least one image; train a second AI model based on second training data comprising sets of imaging biomarker features associated with task-specific labels, the second AI model trained to identify at least one task-specific feature based at least partially on a set of imaging biomarker features; process at least one input image with the first AI model to generate a first AI model output; and process the first AI model output with the second AI model to generate a second AI model output.

In non-limiting embodiments or aspects, each imaging biomarker feature of the plurality of imaging biomarker features comprises at least one value corresponding to a specific aspect of the at least one image or video including the at least one image. In non-limiting embodiments or aspects, the first AI model output comprises a set of imaging biomarker features, and the second AI model output comprises at least one task-specific feature. In non-limiting embodiments or aspects, the task-specific labels comprise severity metrics. In non-limiting embodiments or aspects, the first AI model is configured to process a sequence of images to identify the plurality of imaging biomarker features. In non-limiting embodiments or aspects, the program instructions cause the at least one computing device to: generate the first training data based on annotations selected from a plurality of options presented on at least one graphical user interface. In non-limiting embodiments or aspects, the program instructions cause the at least one computing device to: generate the second training data based on user input associating the task-specific labels with imaging-biomarker inputs. In non-limiting embodiments or aspects, the second AI model is configured to identify the at least one task-specific feature based at least partially on at least one of the following: the at least one input image, the at least one image, a video including the at least one image, an output of an image or video processing algorithm based on the at least one image or a video including the at least one image, or any combination thereof. In non-limiting embodiments or aspects, the plurality of imaging biomarker features comprises at least one of the following features of at least one ultrasound image: A-line, B-line, pleural line irregularity, or any combination thereof. The computer program product of clause 21, wherein the plurality of imaging biomarkers is predefined.

Further non-limiting embodiments are recited in the following clauses:

Clause 1: A method comprising: training a first artificial intelligence (AI) model based on first training data comprising images labeled with imaging biomarkers, the first AI model trained to identify a plurality of imaging biomarker features in at least one image; training a second AI model based on second training data comprising sets of imaging biomarker features associated with task-specific labels, the second AI model trained to identify at least one task-specific feature based at least partially on a set of imaging biomarker features; processing at least one input image with the first AI model to generate a first AI model output; and processing the first AI model output with the second AI model to generate a second AI model output.

Clause 2: The method of clause 1, wherein each imaging biomarker feature of the plurality of imaging biomarker features comprises at least one value corresponding to a specific aspect of the at least one image or video including the at least one image.

Clause 3: The method of clauses 1 or 2, wherein the first AI model output comprises a set of imaging biomarker features, and wherein the second AI model output comprises at least one task-specific feature.

Clause 4: The method of any of clauses 1-3, wherein the task-specific labels comprise severity metrics.

Clause 5: The method of any of clauses 1-4, wherein the first AI model is configured to process a sequence of images to identify the plurality of imaging biomarker features.

Clause 6: The method of any of clauses 1-5, further comprising: generating the first training data based on annotations selected from a plurality of options presented on at least one graphical user interface.

Clause 7: The method of any of clauses 1-6, further comprising: generating the second training data based on user input associating the task-specific labels with imaging-biomarker inputs.

Clause 8: The method of any of clauses 1-7, wherein the second AI model is configured to identify the at least one task-specific feature based at least partially on at least one of the following: the at least one input image, the at least one image, a video including the at least one image, an output of an image or video processing algorithm based on the at least one image or a video including the at least one image, or any combination thereof.

Clause 9: The method of any of clauses 1-8, wherein the plurality of imaging biomarker features comprises at least one of the following features of at least one ultrasound image: A-line, B-line, pleural line irregularity, or any combination thereof.

Clause 10: The method of any of clauses 1-9, wherein the plurality of imaging biomarkers is predefined.

Clause 11: A system comprising: at least one computing device programmed or configured to: train a first artificial intelligence (AI) model based on first training data comprising images labeled with imaging biomarkers, the first AI model trained to identify a plurality of imaging biomarker features in at least one image; train a second AI model based on second training data comprising sets of imaging biomarker features associated with task-specific labels, the second AI model trained to identify at least one task-specific feature based at least partially on a set of imaging biomarker features; process at least one input image with the first AI model to generate a first AI model output; and process the first AI model output with the second AI model to generate a second AI model output.

Clause 12: The system of clause 11, wherein each imaging biomarker feature of the plurality of imaging biomarker features comprises at least one value corresponding to a specific aspect of the at least one image or video including the at least one image.

Clause 13: The system of clauses 11 or 12, wherein the first AI model output comprises a set of imaging biomarker features, and wherein the second AI model output comprises at least one task-specific feature.

Clause 14: The system of any of clauses 11-13, wherein the task-specific labels comprise severity metrics.

Clause 15: The system of any of clauses 11-14, wherein the first AI model is configured to process a sequence of images to identify the plurality of imaging biomarker features.

Clause 16: The system of any of clauses 11-15, wherein the at least one computing device is further programmed or configured to: generate the first training data based on annotations selected from a plurality of options presented on at least one graphical user interface.

Clause 17: The system of any of clauses 11-16, wherein the at least one computing device is further programmed or configured to: generate the second training data based on user input associating the task-specific labels with imaging-biomarker inputs.

Clause 18: The system of any of clauses 11-17, wherein the second AI model is configured to identify the at least one task-specific feature based at least partially on at least one of the following: the at least one input image, the at least one image, a video including the at least one image, an output of an image or video processing algorithm based on the at least one image or a video including the at least one image, or any combination thereof.

Clause 19: The system of any of clauses 11-18, wherein the plurality of imaging biomarker features comprises at least one of the following features of at least one ultrasound image: A-line, B-line, pleural line irregularity, or any combination thereof.

Clause 20: The system of any of clauses 11-19 wherein the plurality of imaging biomarkers is predefined.

Clause 21: A computer program product comprising at least one non-transitory computer-readable medium including program instructions that, when executed by at least one computing device, cause the at least one computing device to: train a first artificial intelligence (AI) model based on first training data comprising images labeled with imaging biomarkers, the first AI model trained to identify a plurality of imaging biomarker features in at least one image; train a second AI model based on second training data comprising sets of imaging biomarker features associated with task-specific labels, the second AI model trained to identify at least one task-specific feature based at least partially on a set of imaging biomarker features; process at least one input image with the first AI model to generate a first AI model output; and process the first AI model output with the second AI model to generate a second AI model output.

Clause 22: The computer program product of clause 21, wherein each imaging biomarker feature of the plurality of imaging biomarker features comprises at least one value corresponding to a specific aspect of the at least one image or video including the at least one image.

Clause 23: The computer program product of clauses 21 or 22, wherein the first AI model output comprises a set of imaging biomarker features, and wherein the second AI model output comprises at least one task-specific feature.

Clause 24: The computer program product of any of clauses 21-23, wherein the task-specific labels comprise severity metrics.

Clause 25: The computer program product of any of clauses 22-24, wherein the first AI model is configured to process a sequence of images to identify the plurality of imaging biomarker features.

Clause 26: The computer program product of any of clauses 22-25, wherein the program instructions cause the at least one computing device to: generate the first training data based on annotations selected from a plurality of options presented on at least one graphical user interface.

Clause 27: The computer program product of any of clauses 22-26, wherein the program instructions cause the at least one computing device to: generate the second training data based on user input associating the task-specific labels with imaging-biomarker inputs.

Clause 28: The computer program product of any of clauses 22-27, wherein the second AI model is configured to identify the at least one task-specific feature based at least partially on at least one of the following: the at least one input image, the at least one image, a video including the at least one image, an output of an image or video processing algorithm based on the at least one image or a video including the at least one image, or any combination thereof.

Clause 29: The computer program product of any of clauses 22-28, wherein the plurality of imaging biomarker features comprises at least one of the following features of at least one ultrasound image: A-line, B-line, pleural line irregularity, or any combination thereof.

Clause 30: The computer program product of any of clauses 22-29 wherein the plurality of imaging biomarkers is predefined.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the non-limiting, exemplary embodiments that are illustrated in the accompanying drawings, in which:

FIG. 5 illustrates a GUI for annotating images and generating training data according to non-limiting embodiments.

DETAILED DESCRIPTION

Figure 1:
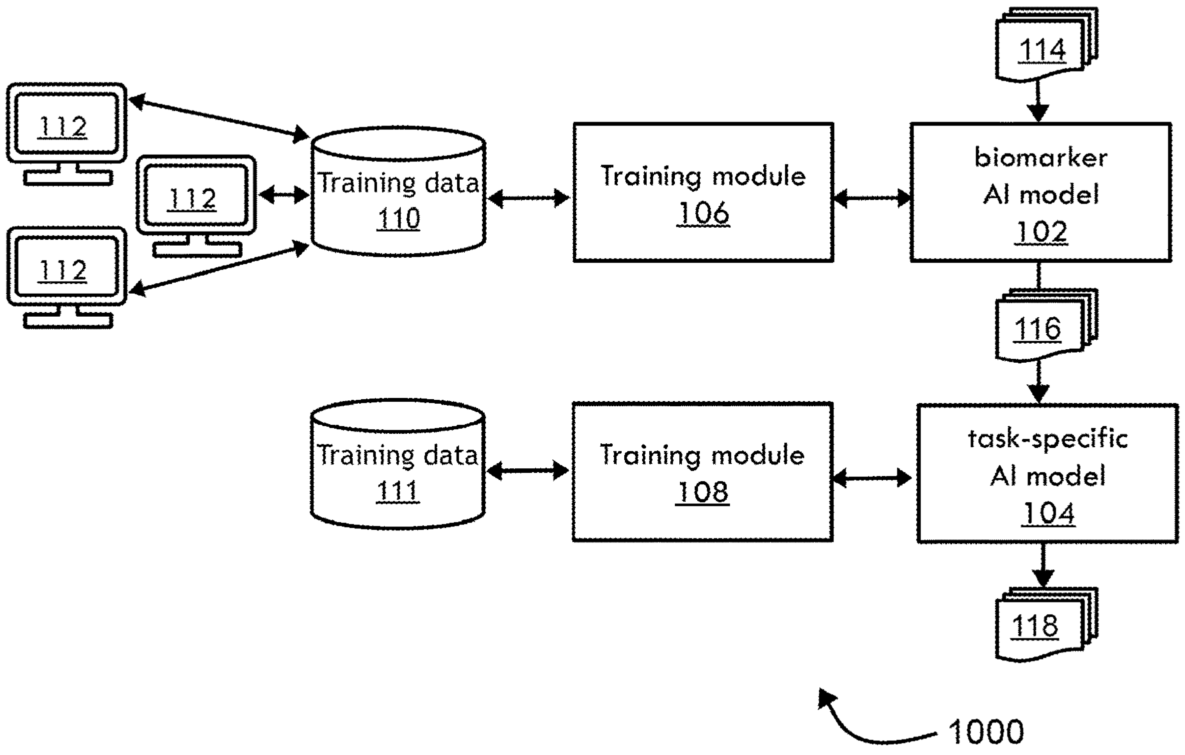
FIG. 1 illustrates a system for extracting features from imaging biomarkers according to non-limiting embodiments.

It is to be understood that the embodiments may assume various alternative variations and step sequences, except where expressly specified to the contrary. It is also to be understood that the specific devices and processes described in the following specification are simply exemplary embodiments or aspects of the disclosure. Hence, specific dimensions and other physical characteristics related to the embodiments or aspects disclosed herein are not to be considered as limiting. No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Also, as used herein, the terms "has," "have," "having," or the like are intended to be open-ended terms. Further, the phrase "based on" is intended to mean "based at least partially on" unless explicitly stated otherwise.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. A computing device may also be a desktop computer or other form of non-mobile computer. In non-limiting embodiments, a computing device may include an AI accelerator, including an application-specific integrated circuit (ASIC) neural engine such as Apple's M1® "Neural Engine" or Google's TENSORFLOW® processing unit. In non-limiting embodiments, a computing device may be comprised of a plurality of individual circuits.

When clinicians interpret point-of-care lung ultrasound (LUS), they identify biomarkers such as A-lines, B-lines, and pleural line thickness and then use these to inform diagnoses and patient care decisions. Likewise, other types of biomarkers may be identified and used in other types of images representing part of an anatomy. Training AI networks to specifically identify and classify these biomarkers can both enhance machine learning and render AI outputs to be relatable to clinicians. Existing ANN approaches train models end-to-end on the downstream task. By nature of this task specific training, the learned features are task-specific and do not readily generalize to other tasks. These task-specific models require retraining or transfer learning to adapt to new end tasks.

Non-limiting embodiments provide for a new and improved system, method, and computer program product for extracting features from imaging biomarkers to provide efficiencies over existing machine-learning systems, such as eliminating a need for retraining and/or applying transfer learning to adapt a biomarker model to new end tasks. Non-limiting embodiments described herein solve technical problems faced by existing machine-learning approaches by separating a diagnostic learning task into first predicting generic visual biomarkers using weak supervision followed by fitting task-specific models (e.g., such as Expert models) on these predicted biomarkers. Decoupling the feature learning from the downstream task enables the model to learn generic features that can readily adapt to new downstream tasks.

In non-limiting embodiments, the biomarkers extracted from the one or more images may be represented as smaller feature vectors (as compared to feature vectors used in multi-layer-perceptron (MLP) classifier models that may use 2-3 fully-connected (FC) layers, each with 1024-4096 or more features). For example, in some non-limiting embodiments, biomarker features of a biomarker may be represented by a predefined number (e.g., such as 38) of scalar values. It will be appreciated that various other configurations are possible. In non-limiting embodiments, each biomarker feature is associated with a specific value (e.g., such as the number of B-lines present in the video, which is an indicator of the severity of the patient). Having a succinct feature representation allows for more efficient training of subsequent AI models (e.g., including Expert models or the like) to perform a variety of end tasks, including future tasks which may not have been originally anticipated when training the first AI model (e.g., the biomarker model). To create training data, these biomarker features may be labeled by annotators (e.g., through GUIs) as attributes of the entire video or entire image, without requiring the label to provide any spatial or temporal specificity (e.g., without requiring additional and/or more complicated inputs) as to where or when in the video or image the biomarker appears, to facilitate faster labeling and the creation of a relatively larger set of training data. In such examples, the spatial-temporal attributes may be learned by the AI model 102 such that the biomarker labels are used to provide weak supervision to train the biomarker model.

Non-limiting embodiments allow for the use of simpler (e.g., more efficient and using fewer computing resources) Expert models, since such models trained on top of a biomarker model as described herein operate on concise biomarker features rather than on image or video space (an extreme dimensionality reduction). Because an Expert model trained on top of the biomarker model is analyzing a much simpler, more apropos representation, it may be trained using less data (with task-specific labels) as compared to the larger amount of data used to train the more complex biomarker model. Thus the training cost of each Expert model is lower than would be experienced with existing Expert models that are trained end-to-end. Accordingly, small amounts of patient-specific or task-specific data might be used to create one or more new AI models by leveraging the capabilities of the biomarker model (which may be learned from a private dataset that was only used to train the biomarker model in some examples).

Further, in some non-limiting embodiments, human annotators may provide simple, discrete (e.g., binary) cues of clinically significant features, without the use of tedious segmentation labels, thus reducing the annotation burden, including the amount of computing resources used to facilitate annotation. These visual semantic biomarker features may be quickly assignable using selectable options on a graphical user interface (GUI), such as checkboxes, by clinical experts. This weak supervision may then be leveraged to ultimately achieve a limited number (e.g., 38 or another amount) of biomarker features, with each biomarker feature having a simple representation (e.g., binary, scalar, or the like). In some non-limiting embodiments, the predicted biomarkers are relatable to clinicians who can readily understand and verify the biomarker model output, which may provide confidence and insight into the immediate inputs of the subsequent diagnostic determinations. Further, in non-limiting embodiments, an Expert model trained on top of a biomarker model as disclosed herein avoids overfitting to spurious correlations in data as a result of the informational "bottleneck" created by training the Expert model only on a set number of biomarker features.

Figure 2:
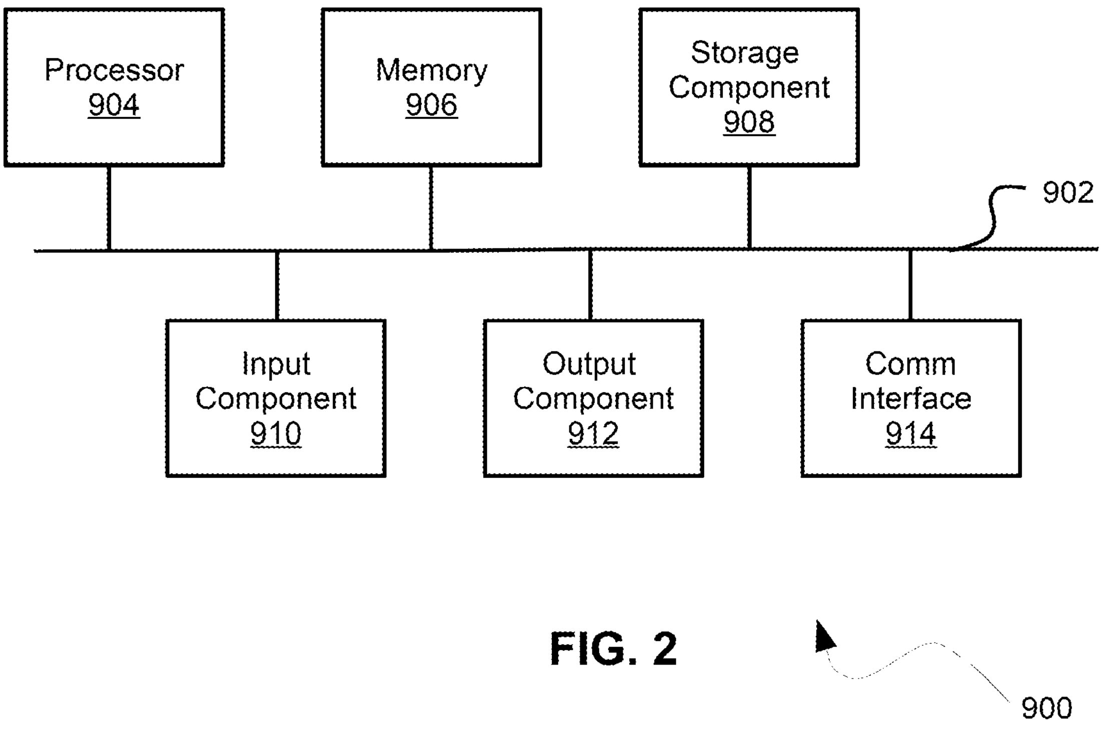
FIG. 2 illustrates example components of a computing device used in connection with non-limiting embodiments.

FIG. 1 shows a system 1000 for extracting features from imaging biomarkers according to non-limiting embodiments. A first AI model 102 (e.g., biomarker model) may be part of and/or executed by a computing device. The first AI model 102 may include, for example, one or more ANNs and/or other type of machine-learning model(s). Although a single first AI model 102 is shown in FIG. 2, it will be appreciated that in some non-limiting embodiments the AI model 102 may include a group of AI models that each output a single biomarker or a subset of the total number of biomarkers. The first AI model 102 may be configured to process, as input, at least one image 114 (e.g., an image, a plurality of images, a video including a sequence of images, and/or the like) and output a plurality of imaging biomarker features 116. In non-limiting embodiments, the first AI model 102 may be configured to process lung ultrasound images, although it will be appreciated that various types of images that include biomarkers may be processed and that the systems and methods described herein are not limited to lungs or ultrasound images.

As used herein, the term "biomarker" refers to a distinctive biological or biologically derived indicator (e.g., relating to a medical process, an event experienced by an individual, a condition experienced by an individual, and/or the like). In the context of lung ultrasound images, for example, biomarkers may include A-lines, B-lines, and distortions of the pleural line, as examples. Biomarkers specific to lungs may also include a "lung point" for pneumothorax and a sonolucent space between the parietal and visceral pleural surfaces for pleural effusion. Different regions of anatomy may be associated with different biomarkers.

As used herein, the term "biomarker feature" refers to a specific feature of a biomarker, such as the presence of one or more A-line(s), a count of A-lines, a thickness (e.g., width) of A-lines, a boldness (e.g. intensity) of A-lines, a shape of an A-line, the presence of a B-line, a count of B-lines, a thickness of B-lines, a shape of a B-line, a pleural line, a thickness of a pleural line, a shape of a pleural line, a location of one or more lines (e.g., A-line(s), B-line(s), pleural line), a location of one or more lines relative to another biomarker, an indent and/or break of a pleural line, a consolidation, an effusion, and/or the like. A biomarker feature may be represented by, for example, a single value that corresponds to a specific aspect of at least one image.

With continued reference to FIG. 1, the system 1000 further includes a second AI model 104 (e.g., a task-specific model) that may be part of and/or executed by a computing device (e.g., the same or different computing device than is used for executing AI model 102). The second AI model 104 may include, for example, an ANN or other type of machine-learning model. The second AI model 104 may be configured to process, as input, the output 116 of the first AI model 102 (e.g., biomarker features for one or more images) and output a task-specific label. In some examples, the second AI model 104 may additionally process, as input, the original one or more images, a video including the one or more images, an output of an image or video processing algorithm based on the one or more images, and/or the like.

Still referring to FIG. 1, a training module 106 may be used to train the first AI model 102. The training module 106 may include, for example, one or more software processes executed by one or more computing devices. For example, in non-limiting embodiments, the first AI model 102 may be trained using a GPU (e.g., a Nvidia RTX A6000 GPU or the like) with a batch size of 4 for 100 epochs. Various other types of hardware and software may be used. The training model 106 may train the AI model 102 based on training data 110 that includes images labeled with predefined imaging biomarkers. In non-limiting embodiments, the training data 110 may be generated based on annotations selected from a plurality of options presented on at least one GUI 112 shown to a plurality of annotators.

As shown in FIG. 1, a second training module 108 may be used to train the second AI model 104. The training module 108 may include, for example, one or more software processes executed by one or more computing devices (e.g., the same or different computing device(s) used to execute training module 106). The training model 108 may train the second AI model 104 based on training data 111 that includes sets of imaging biomarker features associated with task-specific labels. In non-limiting embodiments, the training data 111 used to train the second AI model 104 is generated based on user input associating the task-specific labels with imaging-biomarker inputs. Although only one second AI model 104 is shown in FIG. 1, it will be appreciated that numerous task-specific models may be created and trained using the output of the first AI model 102.

In non-limiting embodiments, one or more AI models (e.g., such as task-specific model 104) may be trained to learn known relationships by learning to predict not only the desired task-specific metrics, but to also predict related metrics that are known or believed to be (potentially) relevant to predicting the desired task-specific metrics. As an example, such task-specific related metrics may include non-imaging biomarkers such as patient vital signs, outcomes, and/or the like. Accordingly, knowledge chains (e.g., relationships) may be created by the AI model 104 that relate visual inputs to known visual features and to known biomarker outputs, all of which are used as an (partial or complete) intermediate basis on which to predict the desired metrics. In some non-limiting embodiments, it is further possible to use explicit (rather than learned) knowledge to specify how the desired metrics should be computed from this intermediate basis (e.g., using directly specified equations, heuristics, decision thresholds, and/or the like). Further, it is also possible to incorporate other modal information readily available (e.g., blood pressure, sugar level, presence of foreign bodies and antibodies in the blood, other blood-test results, and/or the like) with the learned/predicted features in order to predict the desired metrics.

As an example, to predict patient disease severity from lung ultrasound images, AI model 102 may be trained to recognize imaging biomarkers, such as A-lines, B-lines, pleural consolidation(s), pleural-line irregularities, and/or the like, AI model 104 may be trained to predict related non-imaging biomarkers such as blood oxygen ratio, ECG measurements, and/or the like, and then another AI model may be trained to use all of these predictions and features to predict the severity of the lung disease of the patient. In some non-limiting embodiments, it is further possible to explicitly specify an intermediate lung-appearance severity metric using logic (e.g., such as if-then-else rules), such as assigning a lung-appearance severity of 3 if a large pleural consolidation is detected, otherwise assigning a severity of 2 if ≥5 B-lines or a small pleural consolidation is detected, otherwise assigning a severity of 1 if >2 B-lines are detected or A-lines are not detected, and a lung-appearance severity of 0 otherwise. In some examples, these visual biomarker-based features, the lung-appearance severity, the predicted blood oxygen ratio, and the other learned features could all be used as input to a final AI-model component to predict the metric of the overall disease severity of the patient.

Figure 3:
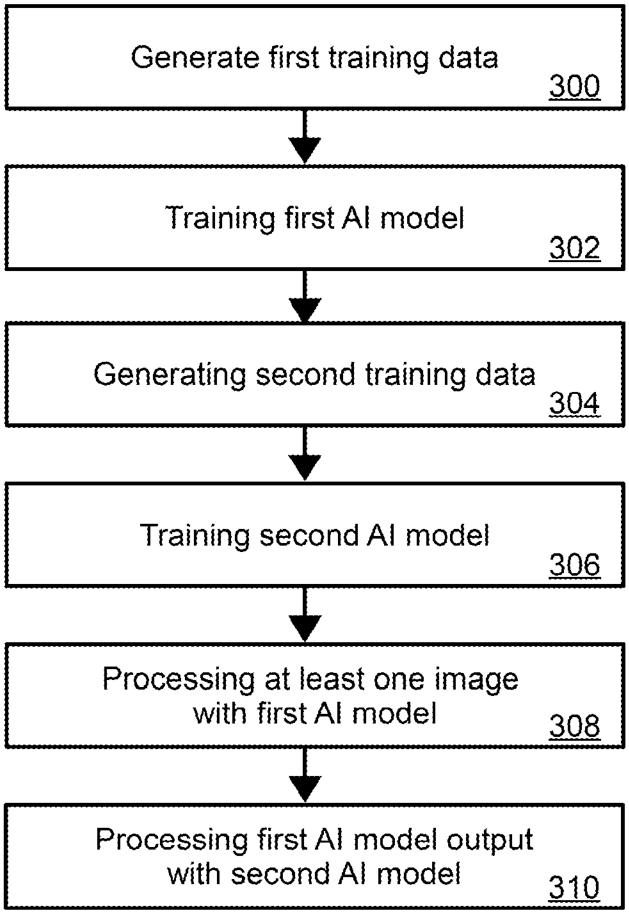
FIG. 3 illustrates a flow diagram for a method of extracting features from imaging biomarkers according to non-limiting embodiments.

Referring now to FIG. 3, a flow diagram is shown for a method of extracting features from imaging biomarkers according to non-limiting embodiments. The steps shown in FIG. 3 are for example purposes only. It will be appreciated that additional, fewer, different, and/or a different order of steps may be used in non-limiting embodiments. At a first step 300, first training data is generated. In non-limiting embodiments, the first training data may be generated through an intuitive, online qualitative annotation tool that may be displayed through a GUI to a human annotator (e.g., such as a trained sonographer) for labeling and scoring. By only prompting annotators to use semantic labels for each of hundreds of videos, a larger quantity of training data can be generated with the amount of resources and time as it would take to draw boundary masks on a much smaller set of data. The GUI 500 shown in FIG. 5 is a non-limiting example of an annotation tool that may be used to label one or more images and/or videos.

At step 302 of FIG. 3, a first AI model (e.g., a biomarker model) is trained based on the training data generated at step 300. The biomarker model may be created in various ways and with various machine-learning techniques. For example, in non-limiting embodiments, the biomarker model may be configured as a residual neural network (ResNet) and incorporate classifiers such as Decision Tree (DT), SVM, Random Forest (RF), AdaBoost (AB), Nearest Neighbors (NN), and MLP classifiers with default parameters. For example, MLP Large in python uses 3 hidden layers (128, 64, 32) with an adaptive learning rate. To handle the randomness in these simple classifiers, a number of models may be fit (e.g., three or another amount) and the best model may be chosen. It will be appreciated that various other machine-learning architectures and techniques may be used.

In non-limiting embodiments, the biomarker model is trained at step 302 to predict the biomarker features (e.g., such as a predefined set of biomarker features) using binary, cross-entropy loss functions. In some non-limiting embodiments, the biomarker model may be trained only once for multiple downstream tasks and/or training multiple secondary AI models. The training may be performed on images that are resized (e.g., to 224×224 pixels or another size) using bilinear interpolation. The training data from step 300 may be augmented using standard augmentations such as, but not limited to, horizontal flipping, pixel intensity scaling (e.g., scales [0.8, 1.1]), image-scaling (e.g., +/−20%), rotation (e.g., +/−15 degrees), and/or translation (e.g., +/−5% pixels). Various types and degrees of augmentations may be used. In non-limiting embodiments, the biomarker model may be trained with a stochastic gradient descent algorithm with an Adam optimizer set with an initial learning rate of 0.0001 to optimize over cross-entropy loss. In non-limiting embodiments, the ReduceLRonPlateau learning rate scheduler (e.g., from PyTorch) is used, which reduces the learning rate by a factor (0.5) when the performance metric (accuracy) plateaus on the validation set. For the final evaluation, the best model from a number of models may be selected with a highest validation set accuracy to test on a set of testing data that was held-out from the training process.

Table 1 shows a non-limiting example of a set of predefined biomarker features and an associated number of sub-categories (e.g., specific biomarker features, such as count, thickness, shape; and/or the like), for a total of 38 features. It will be appreciated that any number of biomarker features may be used.

TABLE 1

| Biomarker Feature | Captured qualitative characteristics | Sub-categories |
|---|---|---|
| A-line | signifies A-line strength and spread | 5 |
| B-line | signifies number of B-lines and type (coalescing or white lung) | 5 |
| B-line origin | signifies whether B-lines originate at pleura or sub-pleura | 3 |
| Pleural line thickness | signifies the thickness of the pleural line | 4 |
| Pleural line location | signifies the pleural line location in the image | 3 |
| Pleural indents | signifies the indentations in the pleural line | 5 |
| Pleural breaks | signifies the breaks in the pleural line | 5 |
| Consolidation | signifies the size of consolidation | 5 |
| Effusion | signifies the size of effusion | 3 |

At step 304, second training data is generated and used at step 306 to train a second AI model. For example, the second AI model may include a classifier model, an Expert model, and/or another model configured to output task-specific labels based on an input of biometric features (e.g., based on an output of the first AI model). In some examples, multiple models may be trained on top of the first AI model, such as but not limited to a task-specific model for modeling lung-severity, a task-specific model for modeling an S/F ratio (the ratio between measured blood oxyhemoglobin saturation(S) and the fraction of inspired oxygen (F)), and/or a task-specific model for modeling a disease category. In some non-limiting examples, the training data generated at step 304 may be based on user input associating task-specific labels with biomarkers. For example, an annotation tool or some other input mechanism may be provided to label a set of biomarker features. In some examples, the second training data may be obtained through the same annotation process that is used to generate the first training data at step 300 (e.g., task-specific labels may be obtained at the same time or through a separate process).

As an example, a task-specific model for modeling lung severity may include a number of lung-severity classes (e.g., a score of 0 indicates a normal lung with increasing values associated with increasing severity). As another example, a task-specific model for modeling an S/F ratio may include a number of ranges as classes (e.g., [>430, 275 430, 180 275, <180]). These reflect the maximum that the following devices are able to support lungs in oxygenating blood: ambient air, standard nasal cannula, venturi mask, and more intensive oxygen delivery devices only available in intensive care settings (e.g. non-invasive mechanical ventilation, invasive mechanical ventilation), respectively. As a further example, a task-specific model for modeling a disease category based on lung ultrasound images may classify a patient based on their biomarker(s) as one of the following categories: Healthy, COVID Pneumonia, Interstitial Lung Disease, Asthma/COPD Exacerbation, Cardiogenic Pulmonary Edema, Other lung diseases, and Other non-lung diseases. These diseases are representative examples of pulmonary pathologies encountered in the inpatient clinical setting of a hospital. Each disease imposes disease-specific changes to the physical architecture of lung parenchyma.

With continued reference to FIG. 3, after the second AI model is trained at step 306, the trained first model and trained second model may be used to process data. Such processing may be seamless for an end-user. For example, at step 308, at least one image (e.g., a single image, a video including a sequence of images, and/or the like) may be input into the first AI model to generate a set of biomarker features. In non-limiting embodiments, the image may be from a lung ultrasound, although various types of images showing biological features of an anatomy may be used. At step 310, the biomarker features output by the first AI model may be automatically input into one or more second AI models (e.g., task-specific models). In addition to receiving the output of the first AI model as input, in non-limiting embodiments the second AI model(s) may also process, as input, the original one or more images, a video including the one or more images, an output of an image or video processing algorithm based on the one or more images, and/or the like.

Figure 4:
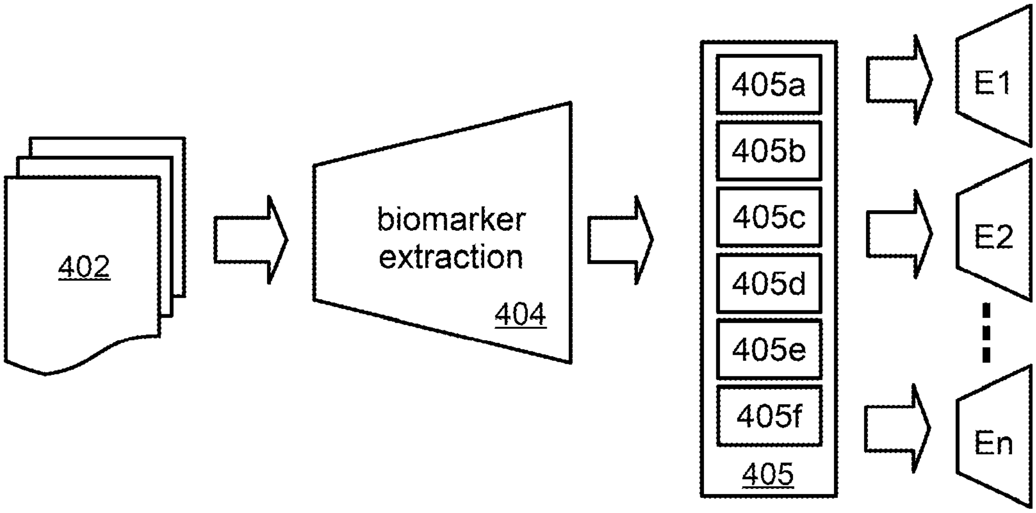
FIG. 4 illustrates a flow diagram for a method of extracting features from imaging biomarkers according to non-limiting embodiments.

Referring now to FIG. 4, a flow diagram is shown for a method of extracting features from imaging biomarkers according to non-limiting embodiments. Images 402 (e.g., such as but not limited to a lung ultrasound video) are input into a biomarker extraction process 404, which may include processing the images 402 with a biomarker model (e.g., the first AI model 102 shown in FIG. 1) that has been trained once and is configured to output a vector 405 of scalar biomarker features 405*a-f*. The biomarker features 405*a-f* are used to train Expert models E1, E2 . . . . En or other task-specific models. It will be appreciated that the illustration in FIG. 4 is for example purposes only and that additional steps and/or modules may be incorporated into the process to augment, adjust, normalize, and/or process any of the data.

Referring now to FIG. 5, a GUI 500 is shown for annotating images and generating training data according to non-limiting embodiments. The example GUI 500 includes a predefined set of biomarker features (e.g., 38 biomarker features) represented with checkboxes. It will be appreciated that various selectable options (e.g., buttons, links, sliders, and/or the like) may be used in addition or alternative to the checkboxes. The GUI 500 may be configured to solicit rapid input from a human annotator with a limited amount of action (e.g., clicking on a checkbox or the like) needed.

Non-limiting embodiments described herein help to improve the interpretability of AI models and to build trust and confidence in the AI model predictions, which is important for safety-critical AI models. Non-limiting embodiments of the systems and methods described herein are also extensible to other modalities, such as audio, text, and/or the like, and is not limited to images.

Embedding Rules and/or Heuristics into an Algorithmic Analysis

In non-limiting embodiments, provided are systems, methods, and computer program products for embedding rules and/or heuristics into an algorithmic analysis of image(s) and/or video(s). A major limiting factor of existing AI-driven systems used in support of medical imaging applications is a strong dependency on large amounts of labelled training data. In non-limiting embodiments, this may be addressed by applying and tailoring interactive weak supervision methodology to medical imaging tasks. This approach combines small amounts of noisy training data and high-level (e.g., image-level) domain-knowledge-driven rules to obtain signals for learning of low-level image features. It enables one to train AI model-based algorithms for image segmentation and/or classification via a combination of commonly used medical heuristics and only small amounts of labeled data relative to existing AI-driven systems.

In non-limiting embodiments, class activation maps may be used for obtaining low-level image features from the high-level medical image heuristics. By obtaining multiple expert clinician-provided rules, and using a neural network model, the specific regions of the image that present the most discriminative features corresponding to the high-level rules can be determined. The power of class activation maps is thus leveraged with the flexibility and convenience of noisy image-level labels for highlighting the desired semantic regions of the ultrasound images (e.g., arteries, veins, and/or the like). For example, to train a ligament segmentation model, doctors define domain rules such as the expected number of ligaments, compressibility of ligaments, hyperechoic shading, temporal consistency of ligaments, and/or the like. This information, in addition to any available labeled data, may be used in non-limiting embodiments to efficiently train a model for ligament segmentation. More specifically, this information and approach leverages the high-level domain rules, which do not require expensive localization information, to highlight the necessary discriminative regions of the data. Non-limiting embodiments result in a drastic reduction of resources needed to develop and deploy AI-driven medical imaging tools in practice.

Figure 6:
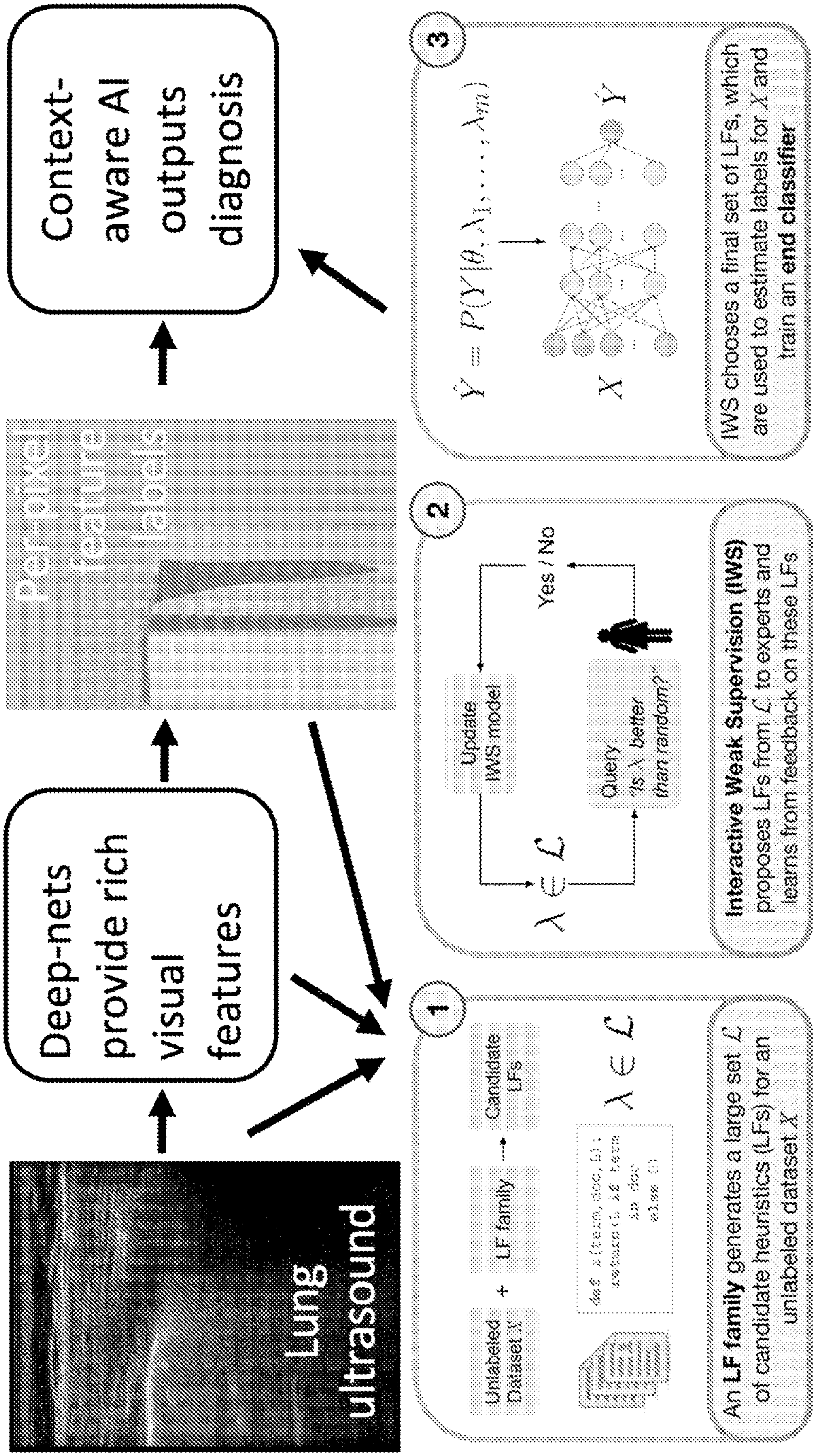
FIG. 6 illustrates a flow diagram for a system and method for embedding rules and/or heuristics into an algorithmic analysis of at least one image according to non-limiting embodiments.

In non-limiting embodiments, a method for embedding rules and/or heuristics into an algorithmic analysis of image(s) and/or video(s) may include the following steps:

(1) Hand label structures and features in a small dataset, including extensive pixel-level annotations;

(2) Train an AI model to output pixel-level labels for the structures of interest, as well as output a rich set of image-feature primitives across scales, suitable for use in clinician-provided heuristics for image classification;

(3a) Automatically generate an initial set of heuristic rules by training an AI model with transfer learning to utilize anatomic-and-appearance relationships between image-feature primitives via graphical models (AAAR-GM), such that AAAR-GM approximately replicates structural outputs. Additionally or alternatively, (3b) directly obtain an initial set of heuristic rules from clinicians using a weak supervision system as described herein;

(4) Provide an interactive GUI to clinicians to facilitate them to modify the relationships in graphical models using visual tools to better match the clinician's predefined notions and expectations (e.g., background clinical knowledge), with live feedback in the GUI showing how their revised graphical models are reinterpreting the images;

(5) Deploy clinician-approved and/or modified graphical models over multi-scale image-feature primitives as the first version of a complete AI model for internal validation;

(6) Utilize feature-activation maps to automatically explain the AI decision process, with human evaluation of the quality of the explanations; and/or (7) Iteratively revise the AI model and the training processes;

It will be appreciated that additional, fewer, different, and/or a different order of steps may be used in non-limiting embodiments. Referring to FIG. 6, a flow diagram is shown for a system and method for embedding rules and/or heuristics into an algorithmic analysis of image(s) and/or video(s) according to non-limiting embodiments.

In non-limiting embodiments, self-supervised representation learning may be used to implement an AI model. Self-supervised representation learning is a method in which unlabeled data is used to learn good representations without direct supervision. The model aims to solve tasks to fill in missing information via "pretext" tasks, thereby learning helpful feature representations for downstream tasks. In examples in which contrastive learning losses are used for pre-training deep learning models, the deep learning model is typically trained on image data and augmented versions of such data with the goal being to compare and contrast them for learning useful features. In pretext tasks where cropping is used, it is possible that images without the primary object present are used for comparisons, which could produce harmful features. A similar issue exists with ultrasound imaging. Thus, in some non-limiting embodiments, to implement self-supervised learning, the system identifies and concretely defines a set amount of rules (a small amount of rules) based on domain knowledge to achieve good cropping for pretext tasks in the ultrasound image domain. Rules may seek to prevent cropping of regions with pulsating elements, as an example, to preserve relevant features. In non-limiting embodiments, various heuristics may be combined to avoid cropping hyperechoic or hypoechoic regions, as those will most likely be important anatomical structures. Heuristic rules may prevent cropping out critical classes in the data to reduce the likelihood of learning harmful feature representations.

In non-limiting embodiments of a self-supervised learning method, the system identifies useful transformations and augmentations which make better use of the ultrasound image features. For example, one pretext task could including splitting the ultrasound images into different-sized regions and using the act of reorganizing the image blocks as the pretext task with the goal of learning useful features which represent the proper arrangement of anatomical structures. Pretext tasks could also be designed around the temporal nature of ultrasound images to predict or leverage motion information across the frames to learn potentially useful information for downstream tasks.

In non-limiting embodiments, the system may embed user-input heuristics directly into self-supervised learning tasks and additional methods via the usage of a framework similar to data programming. This approach could directly input easily interpretable medical heuristics, generate probabilistic labels which take into consideration the relationships among the heuristics, and then use those labels for more intelligent training methods. Embedding critical medical heuristics within each of the aforementioned training methods may better utilize the knowledge and time of clinicians while developing more intelligent, robust, and data-efficient methods for ultrasound segmentation.

Referring now to FIG. 2, shown is a diagram of example components of a computing device 900 for implementing and performing the systems and methods described herein according to non-limiting embodiments. In some non-limiting embodiments, device 900 may include additional components, fewer components, different components, or differently arranged components than those shown. Device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 2, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method comprising:

training a first artificial intelligence (AI) model based on first training data comprising images labeled with imaging biomarkers, the first AI model trained to identify a plurality of imaging biomarker features in at least one image;

training a second AI model based on second training data comprising sets of imaging biomarker features associated with task-specific labels, the second AI model trained to identify at least one task-specific label based at least partially on a set of imaging biomarker features;

processing at least one input image with the first AI model to generate a first AI model output, the first AI model output comprising a set of imaging biomarker features from the at least one input image; and processing the first AI model output with the second AI model to generate a second AI model output, the second AI model output comprising at least one task-specific label for the set of imaging biomarker features from the at least one input image.

2. The method of claim 1, wherein each imaging biomarker feature of the plurality of imaging biomarker features comprises at least one value corresponding to a specific aspect of the at least one image or video including the at least one image.

3. The method of claim 1, wherein the task-specific labels comprise severity metrics.

4. The method of claim 1, wherein the first AI model is configured to process a sequence of images to identify the plurality of imaging biomarker features.

5. The method of claim 1, further comprising:

generating the first training data based on annotations selected from a plurality of options presented on at least one graphical user interface.

6. The method of claim 1, further comprising:

generating the second training data based on user input associating the task-specific labels with imaging-biomarker inputs.

7. The method of claim 1, wherein the second AI model is configured to identify the at least one task-specific label based at least partially on at least one of the following: the at least one input image, the at least one image, a video including the at least one image, an output of an image or video processing algorithm based on the at least one image or a video including the at least one image, or any combination thereof.

8. The method of claim 1, wherein the plurality of imaging biomarker features comprises at least one of the following features of at least one ultrasound image: A-line, B-line, pleural line irregularity, or any combination thereof.

9. The method of claim 1, wherein the plurality of imaging biomarkers is predefined.

10. A system comprising:

at least one computing device programmed or configured to:

train a first artificial intelligence (AI) model based on first training data comprising images labeled with imaging biomarkers, the first AI model trained to identify a plurality of imaging biomarker features in at least one image;

train a second AI model based on second training data comprising sets of imaging biomarker features associated with task-specific labels, the second AI model trained to identify at least one task-specific label based at least partially on a set of imaging biomarker features;

process at least one input image with the first AI model to generate a first AI model output, the first AI model output comprising a set of imaging biomarker features from the at least one input image; and process the first AI model output with the second AI model to generate a second AI model output, the second AI model output comprising at least one task-specific label for the set of imaging biomarker features from the at least one input image.

11. The system of claim 10, wherein each imaging biomarker feature of the plurality of imaging biomarker features comprises at least one value corresponding to a specific aspect of the at least one image or video including the at least one image.

12. The system of claim 10, wherein the task-specific labels comprise severity metrics.

13. The system of claim 10, wherein the first AI model is configured to process a sequence of images to identify the plurality of imaging biomarker features.

14. The system of claim 10, wherein the at least one computing device is further programmed or configured to:

generate the first training data based on annotations selected from a plurality of options presented on at least one graphical user interface.

15. The system of claim 10, wherein the at least one computing device is further programmed or configured to:

generate the second training data based on user input associating the task-specific labels with imaging-biomarker inputs.

16. The system of claim 10, wherein the second AI model is configured to identify the at least one task-specific feature based at least partially on at least one of the following: the at least one input image, the at least one image, a video including the at least one image, an output of an image or video processing algorithm based on the at least one image or a video including the at least one image, or any combination thereof.

17. The system of claim 10, wherein the plurality of imaging biomarker features comprises at least one of the following features of at least one ultrasound image: A-line, B-line, pleural line irregularity, or any combination thereof.

18. The system of claim 10 wherein the plurality of imaging biomarkers is predefined.

19. A computer program product comprising at least one non-transitory computer-readable medium including program instructions that, when executed by at least one computing device, cause the at least one computing device to:

train a first artificial intelligence (AI) model based on first training data comprising images labeled with imaging biomarkers, the first AI model trained to identify a plurality of imaging biomarker features in at least one image;

train a second AI model based on second training data comprising sets of imaging biomarker features associated with task-specific labels, the second AI model trained to identify at least one task-specific label based at least partially on a set of imaging biomarker features;

process at least one input image with the first AI model to generate a first AI model output, the first AI model output comprising a set of imaging biomarker features from the at least one input image; and process the first AI model output with the second AI model to generate a second AI model output, the second AI model output comprising at least one task-specific label for the set of imaging biomarker features from the at least one input image.

* * * * *